US012698271B2

(12) United States Patent
Brown et al.

(10) Patent No.: US 12,698,271 B2
(45) Date of Patent: Aug. 4, 2026

(54) CRYSTALLINE FORM OF A SHP2 INHIBITOR

(71) Applicant: Array BioPharma Inc., Boulder, CO (US)

(72) Inventors: Katie Keaton Brown, Niwot, CO (US); Aaron Keith Goodwin, Golden, CO (US)

(73) Assignee: Pfizer Inc., New York, NY (US)

( * ) Notice: Subject to any disclaimer, the term of this patent is extended or adjusted under 35 U.S.C. 154(b) by 421 days.

(21) Appl. No.: 18/553,214

(22) PCT Filed: Mar. 30, 2022

(86) PCT No.: PCT/IB2022/052982
§ 371 (c)(1),
(2) Date: Sep. 29, 2023

(87) PCT Pub. No.: WO2022/208408
PCT Pub. Date: Oct. 6, 2022

(65) Prior Publication Data

US 2024/0190843 A1 Jun. 13, 2024

Related U.S. Application Data

(60) Provisional application No. 63/321,902, filed on Mar. 21, 2022, provisional application No. 63/169,340, filed on Apr. 1, 2021.

(51) Int. Cl.

| | |
|---|---|
| ***C07D 401/14*** | (2006.01) |
| ***A61K 31/4184*** | (2006.01) |
| ***A61K 31/437*** | (2006.01) |
| ***A61K 31/506*** | (2006.01) |
| ***A61K 31/53*** | (2006.01) |
| ***A61K 39/00*** | (2006.01) |
| ***C07K 16/28*** | (2006.01) |

(52) U.S. Cl.
CPC ........ *C07D 401/14* (2013.01); *A61K 31/4184* (2013.01); *A61K 31/437* (2013.01); *A61K 31/506* (2013.01); *A61K 31/53* (2013.01); *C07K 16/2863* (2013.01); *A61K 2039/505* (2013.01); *C07B 2200/13* (2013.01)

(58) Field of Classification Search
CPC ................ C07D 401/14; C07D 471/14; A61K 31/4184; A61K 31/437; A61K 31/506; A61K 31/53; A61K 2039/505; C07K 16/2863; A61P 35/00; C07B 2200/13
See application file for complete search history.

(56) References Cited

FOREIGN PATENT DOCUMENTS

WO WO-2020201991 A1 * 10/2010 ......... C07D 491/107

OTHER PUBLICATIONS

Chen, Nature, 535, 2016 (Year: 2016).*
Mainardi, Nature Medicine, 24, 2018 (Year: 2018).*
Zhao, Acta Phamaceutica Sinica B, vol. 9, Iss. 2, 2019 (Year: 2019).*
Aaltonen, Jaakko et al., "Solid form screening—A review", European Journal of Pharmaceutics and Biopharmaceutics, 2009, 23-37, 71.
International Search Report dated Jun. 15, 2022 for International Application No. PCT/IB2022/052982, filed Mar. 30, 2022.
Written Opinion of the International Searching Authority for International Application No. PCT/IB2022/052982, filed Mar. 30, 2022.

* cited by examiner

*Primary Examiner* — Susanna Moore
*Assistant Examiner* — Luisalberto Gonzalez
(74) *Attorney, Agent, or Firm* — Beau Burton

(57) ABSTRACT

This Invention relates to a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1). The invention also relates to pharmaceutical compositions comprising this crystalline form, and to methods of using the crystalline form and such compositions for the treatment of abnormal cell growth, such as cancer, in a mammal.

14 Claims, 3 Drawing Sheets

The peaks marked by # are spinning sidebands

CRYSTALLINE FORM OF A SHP2 INHIBITOR

BACKGROUND OF THE INVENTION

Field of the Invention

The invention relates to a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1), pharmaceutical compositions comprising Form 1, and to methods of using Form 1 and such compositions in the treatment of abnormal cell growth, such as cancer, in mammals, especially humans.

Description of the State of the Art

The compound (S)-1'-(6-((2-amino-3-chloropyridin-4-yl)thio)-1,2,4-triazin-3-yl)-1,3-dihydrospiro[indene-2,4'-piperidin]-1-amine is a SHP2 inhibitor having the formula (I):

(I)

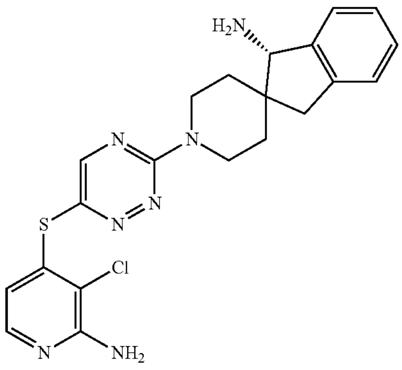

Preparation of (S)-1'-(6-((2-amino-3-chloropyridin-4-yl)thio)-1,2,4-triazin-3-yl)-1,3-dihydrospiro[indene-2,4'-piperidin]-1-amine is disclosed in International Patent Publication WO 2020/201991 (International Application Number PCT/IB2020/053019, published on 8 Oct. 2020), the contents of which are incorporated herein by reference in their entirety.

The present invention provides a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) having desirable properties, such as high crystallinity, high purity and stability.

BRIEF SUMMARY OF THE INVENTION

Each of the embodiments described below can be combined with any other embodiment described herein not inconsistent with the embodiment with which it is combined.

In one aspect, the invention provides a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1). The hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) is characterized by powder X-ray diffraction (PXRD) (2θ).

In another aspect, the invention provides a hemihydrate crystalline (S)-1'-(6-((2-amino-3-chloropyridin-4-yl)thio)-1,2,4-triazin-3-yl)-1,3-dihydrospiro[indene-2,4'-piperidin]-1-amine free base (Form 1) characterized by having a powder X-ray diffraction (PXRD) pattern (2θ) comprising: (a) one, two, three, four, five or more than five peaks selected from the group consisting of the peaks in Table 1 in °2θ±0.2°2θ; (b) one, two, three or four peaks selected from the group consisting of the peaks in Table 1 in °2θ±0.2°2θ; (c) one, two, three, four, five or more than five peaks selected from the group consisting of the peaks in Table 2 in °2θ±0.2°2θ; (d) one, two, three or four peaks selected from the group consisting of the peaks in Table 2 in °2θ±0.2°2θ; or (e) peaks at 2θ values essentially the same as shown in FIG. 1.

In another aspect, the invention provides a pharmaceutical composition comprising a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1), according to any of the embodiments, and at least one pharmaceutically acceptable excipient. In some embodiments, the pharmaceutical composition comprises two or more pharmaceutically acceptable excipients.

In another aspect, the invention provides a method of treating abnormal cell growth in a mammal, including a human, comprising administering to the mammal a therapeutically effective amount of a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1), according to any of the aspects or embodiments described herein.

In another aspect, the invention provides use of a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1), or a pharmaceutical composition comprising a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1), according to any of the aspects or embodiments described herein, in a method of treating abnormal cell growth in a mammal. In yet another aspect, the invention provides use of a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1), according to any of the aspects or embodiments described herein, in the manufacture of a medicament for the treatment of abnormal cell growth in a mammal.

In another aspect, the invention provides a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1), according to any of the aspects or embodiments described herein, for use in a method of treating abnormal cell growth in a mammal.

In frequent embodiments, the abnormal cell growth is cancer. In one embodiment, the abnormal cell growth is cancer mediated by SHP2.

DETAILED DESCRIPTION OF THE INVENTION

Figure 1:
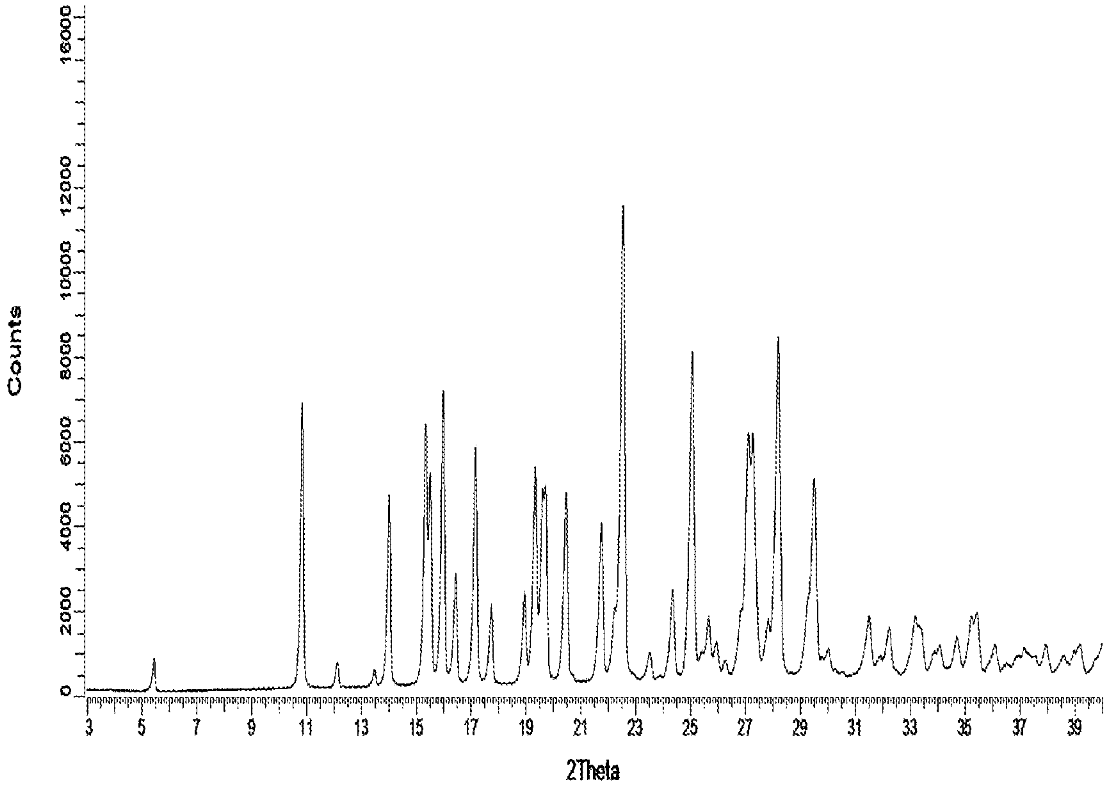
FIG. 1 shows a PXRD pattern of a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1).

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art. In the event that one or more of the incorporated literature and similar materials differs from or contradicts this application, including but not limited to defined terms, term usage, described techniques, or the like, this application controls.

Definitions

As used herein, the singular form "a", "an", and "the" include plural references unless indicated otherwise. For example, "a" substituent includes one or more substituents.

The term "about" means having a value falling within an accepted standard of error of the mean, when considered by one of ordinary skill in the art.

As used herein, the term "essentially the same" means that variability typical for a particular method is taken into account. For example, with reference to X-ray diffraction peak positions, the term "essentially the same" means that typical variability in peak position and intensity are taken into account. One skilled in the art will appreciate that the peak positions (2θ) will show some variability, typically as much as ±0.2°. Further, one skilled in the art will appreciate that relative peak intensities will show inter-apparatus variability, as well as variability due to the degree of crystallinity, preferred orientation, prepared sample surface, and other factors known to those skilled in the art and should be taken as qualitative measures only.

The term "crystalline" as used herein, means having a regularly repeating arrangement of molecules or external face planes. Crystalline forms may differ with respect to thermodynamic stability, physical parameters, x-ray structure and preparation processes.

The term "hemihydrate" means a hydrate in which there are two molecules of the compound, in this case (S)-1'-(6-((2-amino-3-chloropyridin-4-yl)thio)-1,2,4-triazin-3-yl)-1,3-dihydrospiro[indene-2,4'-piperidin]-1-amine free base, for each molecule of water.

The term "substantially pure" means a particular crystalline form includes less than 10%, preferably less than 5%, preferably less than 3%, preferably less than 1% by weight of any other physical forms of the compound.

Crystalline (S)-1'-(6-((2-amino-3-chloropyridin-4-yl)thio)-1,2,4-triazin-3-yl)-1,3-dihydrospiro[indene-2,4'-piperidin]-1-amine Free Base (Form 1)

In one embodiment, the invention provides a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1). The crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) is a hemihydrate. The methods described herein provide a hemihydrate crystalline (S)-1'-(6-((2-amino-3-chloropyridin-4-yl)thio)-1,2,4-triazin-3-yl)-1,3-dihydrospiro[indene-2,4'-piperidin]-1-amine free base (Form 1) which is substantially pure and free of alternative forms. In another embodiment, the invention provides a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) which is substantially pure and free of alternative forms. In one embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) is greater than 95% substantially pure. In one embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) is greater than 97% substantially pure. In one embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) is greater than 99% substantially pure.

The hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) of the present invention is characterized by: (1) a PXRD pattern comprising characterizing peaks at 2θ value of 10.9, 14.0, 15.4, and 16.0°2θ±0.2°2θ; or (2) a $^{13}C$ ssNMR spectrum comprising resonance (ppm) values of 44.4, 47.7, 149.2 and 36.6 ppm±0.2 ppm; or (3) a FT-Raman spectrum comprising wavenumber ($cm^{-1}$) values of 607, 1462, 1051 and 1573 $cm^{-1}$±0.2 $cm^{-1}$. The hemihydrate crystalline form of the present invention may also provide a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1), characterized by two of: (1) a PXRD pattern comprising characterizing peaks at 2θ value of 10.9, 14.0, 15.4, and 16.0±0.2°2θ; (2) a $^{13}C$ ssNMR spectrum comprising resonance (ppm) values of 44.4, 47.7, 149.2 and 36.6±0.2 ppm; or (3) a FT-Raman spectrum comprising wavenumber ($cm^{-1}$) values of 607, 1462, 1051 and 1573±0.2 $cm^{-1}$. The hemihydrate crystalline form of the present invention may further provide a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1), characterized by: (1) a PXRD pattern comprising characterizing peaks at 2θ value of 10.9, 14.0, 15.4, and 16.0±0.2°2θ; (2) a $^{13}C$ ssNMR spectrum comprising resonance (ppm) values of 44.4, 47.7, 149.2 and 36.6±0.2 ppm; and (3) a FT-Raman spectrum comprising wavenumber ($cm^{-1}$) values of 607, 1462, 1051 and 1573±0.2 $cm^{-1}$.

In more further embodiments, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising a peak at 2θ value of 10.9±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising a peak at 2θ value of 16.0±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising a peak at 2θ value of 14.0±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising a peak at 2θ value of 15.4±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising a peak at 2θ value of 15.5±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising a peak at 2θ value of 25.1±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising a peak at 2θ value of 20.5±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising a peak at 2θ value of 29.5±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 10.9 and 16.0±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 10.9 and 14.0±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 10.9 and 15.4±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 16.0 and 14.0±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 16.0 and 15.4±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 14.0 and 15.4±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 10.9, 16.0 and 14.0±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 10.9, 16.0 and 15.4±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 16.0, 14.0 and 15.4±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 10.9, 16.0 and 15.4±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 10.9, 16.0, 14.0 and 15.4±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 10.9, 16.0, 14.0, 15.4 and 15.5±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 10.9, 16.0, 14.0, 15.4, 15.5 and 25.1±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 10.9, 16.0, 14.0, 15.4, 15.5, 25.1 and 20.5±0.2°2θ. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a PXRD pattern comprising peaks at 2θ value of 10.9, 16.0, 14.0, 15.4, 15.5, 25.1, 20.5 and 29.5±0.2°2θ.

In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has PXRD pattern (2θ) comprising: (a) one, two, three, four, five or more than five peaks selected from the group consisting of the peaks in Table 1 in °2θ±0.2°2θ; (b) one, two, three or four peaks selected from the group consisting of the peaks in Table 1 in °2θ±0.2°2θ; (c) one, two, three, four, five or more than five peaks selected from the group consisting of the peaks in Table 2 in °2θ±0.2°2θ; (d) one, two, three or four peaks selected from the group consisting of the peaks in Table 2 in °2θ±0.2°2θ; or (e) peaks at 2θ values essentially the same as shown in FIG. 1.

In more further embodiments, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a $^{13}C$ ssNMR spectrum comprising resonance (ppm) values of 44.4±0.2 ppm. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a $^{13}C$ ssNMR spectrum comprising resonance (ppm) values of 47.7±0.2 ppm. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a $^{13}C$ ssNMR spectrum comprising resonance (ppm) values of 149.2±0.2 ppm. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a $^{13}C$ ssNMR spectrum comprising resonance (ppm) values of 36.6±0.2 ppm. In a further embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a $^{13}C$ ssNMR spectrum comprising resonance (ppm) values of 26.9±0.2 ppm.

Figure 2:
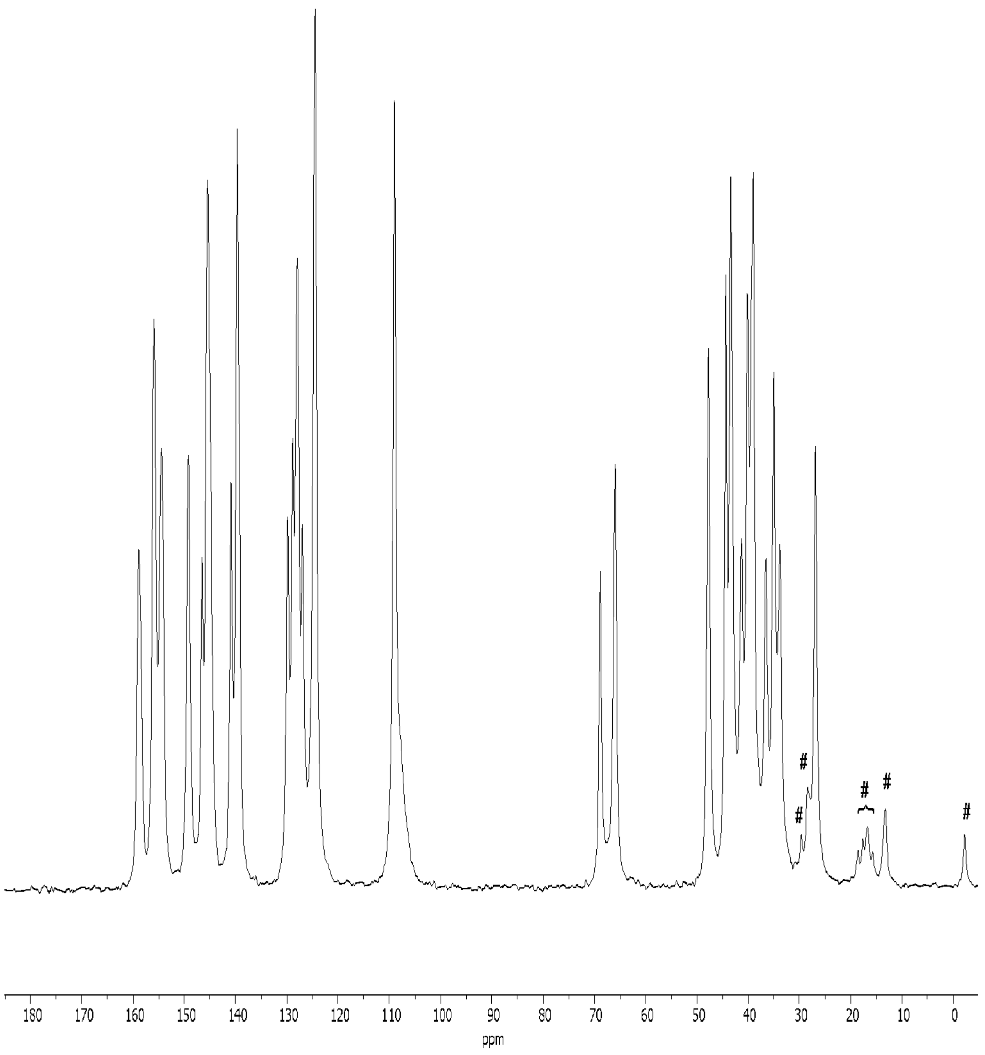
FIG. 2 shows a $^{13}C$ ssNMR spectrum of a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1).

In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has $^{13}C$ ssNMR spectrum (ppm) comprising: (a) one, two, three, four, five or more than five resonance values selected from the group consisting of the values in Table 3 in ppm±0.2 ppm; (b) one, two, three or four resonance values selected from the group consisting of the values in Table 3 in ppm±0.2 ppm; (c) the resonance values in Table 3 in ppm±0.2 ppm; or (d) values (ppm) essentially the same as shown in FIG. 2.

In more further embodiments, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a FT-Raman spectrum comprising wavenumber ($cm^{-1}$) value of 607±0.2 $cm^{-1}$. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a FT-Raman spectrum comprising wavenumber ($cm^{-1}$) value of 1462±0.2 $cm^{-1}$. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a FT-Raman spectrum comprising wavenumber ($cm^{-1}$) value of 1051±0.2 $cm^{-1}$. In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has a FT-Raman spectrum comprising wavenumber ($cm^{-1}$) value of 1573±0.2 $cm^{-1}$.

Figure 3:
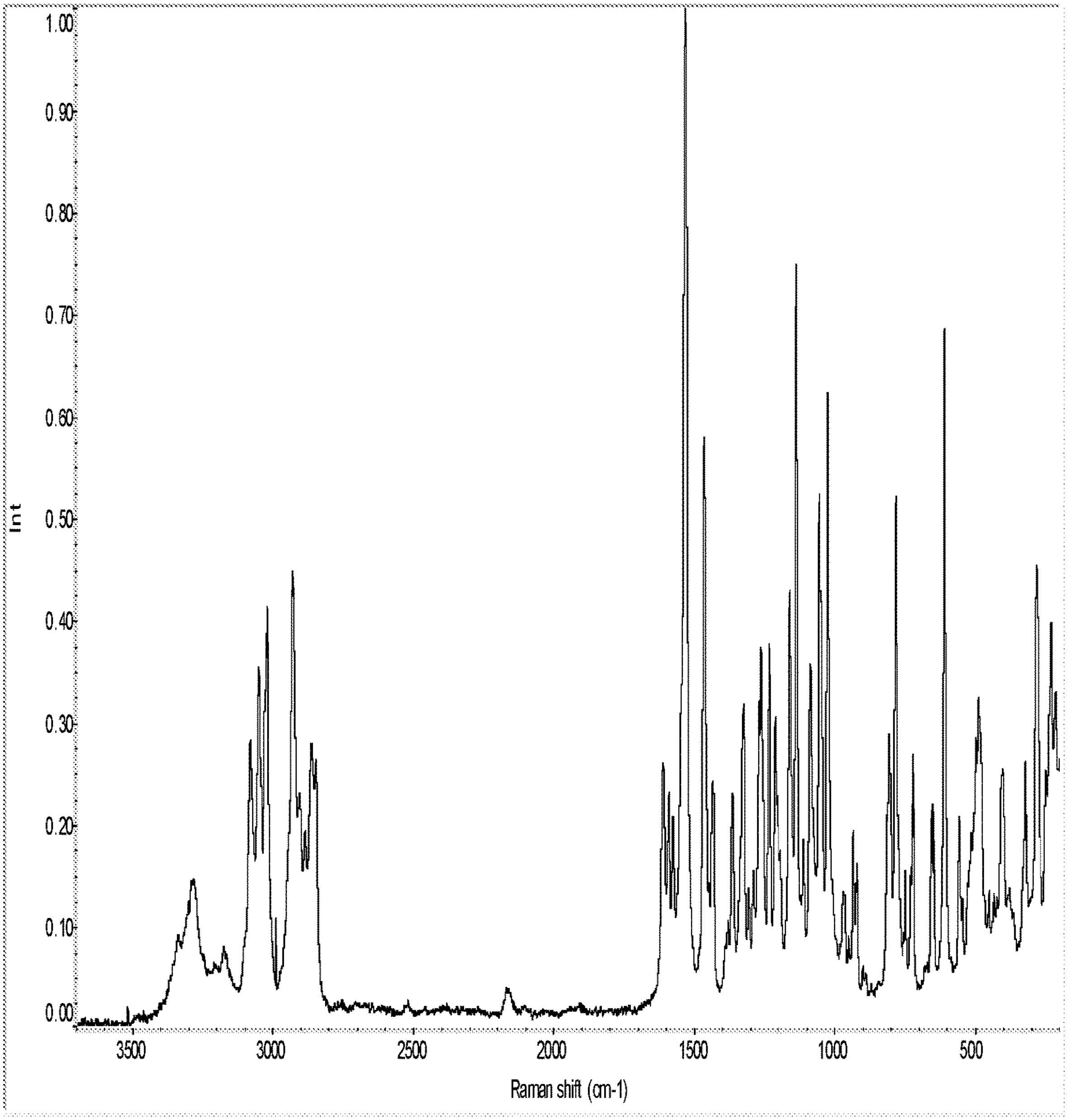
FIG. 3 shows a PXRD pattern of a hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1).

In another embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) has FT-Raman spectrum ($cm^{-1}$) comprising: (a) one, two, three, four, five or more than five wavenumber ($cm^{-1}$) values selected from the group consisting of the values in Table 4 in $cm^{-1}$±0.2 $cm^{-1}$; (b) one, two, three or four wavenumber ($cm^{-1}$) values selected from the group consisting of the values in Table 4 in $cm^{-1}$±0.2 $cm^{-1}$; (c) the wavenumber ($cm^{-1}$) values in Table 4 in $cm^{-1}$±0.2 cm 1; (d) one, two three of four of the wavenumber ($cm^{-1}$) values selected from the group consisting of the wavenumber values in Table 5 in $cm^{-1}$±0.2 $cm^{-1}$; or (d) wavenumber ($cm^{-1}$) values essentially the same as shown in FIG. 3.

In another embodiment, the invention provides a pharmaceutical composition comprising the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) according to any of the embodiments described herein, and at least one pharmaceutically acceptable excipient.

A typical formulation or composition is prepared by mixing a compound described herein and an excipient. Suitable excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005, the disclosures of which are herein incorporated by reference.

"Pharmaceutical composition", as used herein, means the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) according to any of the embodiments described herein as an active ingredient, and at least one pharmaceutically acceptable excipient.

"Pharmaceutically acceptable carrier", as used herein, means a carrier or diluent that does not cause significant irritation to an organism and does not abrogate the biological activity and properties of the administered compound.

Administration of the pharmaceutical composition may be affected by any method that enables delivery of the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) to the site of action. These methods include oral routes, intraduodenal routes, parenteral injection (including intravenous, subcutaneous, intramuscular, intravascular or infusion), topical, and rectal administration.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

In another embodiment, the invention provides method of treating abnormal cell growth in a mammal, preferably a human, comprising administering to the mammal a therapeutically effective amount of the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) according to any of the embodiments described herein.

In another embodiment, the invention provides method of treating abnormal cell growth in a mammal, preferably a human, comprising administering to the mammal a therapeutically effective amount of a pharmaceutical composition comprising the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) according to any of the embodiments described herein.

In another embodiment, the invention the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) according to any of the embodiments described herein for use in treating abnormal cell growth in a mammal, preferably a human.

In another embodiment, the invention provides the use of the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) according to any of the embodiments described herein in treating abnormal cell growth in a mammal, preferably a human.

In another embodiment, the invention provides use of the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) according to any of the embodiments described herein in the manufacture of a medicament for use in a treating abnormal cell growth in a mammal, preferably a human.

In another embodiment, the invention provides the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1), according to any of the aspects or embodiments described herein, for use in therapy.

In another embodiment, the invention provides the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1), according to any of the aspects or embodiments described herein, for use in a method of treating abnormal cell growth in a mammal.

In frequent embodiments of the methods provided herein, the abnormal cell growth is cancer. "Cancer", as used herein, means the physiological condition in mammals that is typically characterized by abnormal or unregulated cell growth. Cancer includes solid tumors named for the type of cells that form them, cancer of blood, bone marrow, or the lymphatic system. Examples of solid tumors include sarcomas and carcinomas. Cancers of the blood include, but are not limited to, leukemia, lymphoma and myeloma. Cancer also includes primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of a different type from the latter one.

In some embodiments, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

"Ameliorating", as used herein, means a lessening or improvement of one or more symptoms upon treatment with a combination described herein, as compared to not administering the combination. Ameliorating also includes shortening or reduction in duration of a symptom.

As used herein, an "effective dosage" or "effective amount" of drug, compound or pharmaceutical composition is an amount sufficient to affect any one or more beneficial or desired, including biochemical, histological and/or behavioral symptoms, of the disease, its complications and intermediate pathological phenotypes presenting during development of the disease. For therapeutic use, a "therapeutically effective amount" refers to that amount of a compound being administered that will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, (4) relieving to some extent (or, preferably, eliminating) one or more signs or symptoms associated with the cancer, (5) decreasing the dose of other medications required to treat the disease, and/or (6) enhancing the effect of another medication, and/or (7) delaying the progression of the disease in a patient.

"Mammal", as used herein, means a warm-blooded animal that has or is at risk of developing a disease described herein and includes, but is not limited to, guinea pigs, dogs, cats, rats, mice, hamsters, and primates, including humans.

"Subject", as used herein, means a human or animal subject. In one embodiment, the subject is a mammal. In a preferred embodiment, the subject is a human.

"Treat" or "treating", as used herein, means to administer a compound of Formula (I) to a subject having the condition to be treated to achieve at least one positive therapeutic effect. For example, treating cancer means to administer a compound of Formula (I) to a subject having cancer, or diagnosed with cancer, to achieve at least one positive therapeutic effect, such as, for example, reduced number of cancer cells, reduced tumor size, reduced rate of cancer cell infiltration into peripheral organs, or reduced rate of tumor metastases or tumor growth, reversing, alleviating, inhibiting the progress of, or preventing the disorder or condition to which such term applies, or one or more symptoms of such disorder or condition. The term "treatment", as used herein, unless otherwise indicated, means the act of treating as "treating" is defined immediately above. The term "treating" also includes adjuvant and neo-adjuvant treatment of a subject.

In some embodiments, the treatment achieved by a compound of Formula (I) is defined by reference to any of the following: partial response (PR), complete response (CR), overall response (OR), progression free survival (PFS), disease free survival (DFS) and overall survival (OS). PFS, also referred to as "Time to Tumor Progression" indicates the length of time during and after treatment that the cancer does not grow and includes the amount of time patients have experienced a CR or PR, as well as the amount of time patients have experienced stable disease (SD). DFS refers to the length of time during and after treatment that the patient remains free of disease. OS refers to a prolongation in life expectancy as compared to naïve or untreated subjects or patients. In some embodiments, response to a combination of the invention is any of PR, CR, PFS, DFS, OR or OS that is assessed using Response Evaluation Criteria in Solid Tumors (RECIST) 1.1 response criteria.

In one embodiment, the abnormal cell growth disease is cancer. In one embodiment, the cancer may be selected from melanoma, juvenile myelomoncytic leukemias, neuroblastoma, Philadelphia chromosome positive chronic myeloid, Philadelphia chromosome positive acute lymphoblastic leukemias, acute myeloid leukemias, myeloproliferative neoplasms (such as Polycythemia Vera, Essential Thrombocythemia and Primary Myelofibrosis), breast cancer, lung cancer, liver cancer, colorectal cancer, esophageal cancer, gastric cancer, squamous-cell carcinoma of the head and neck, glioblastoma, anaplastic large-cell lymphoma, thyroid carcinoma, and spitzoid neoplasms. In one embodiment, the cancer is melanoma. In one embodiment, the cancer is juvenile myelomoncytic leukemias. In one embodiment, the cancer is neuroblastoma. In one embodiment, the cancer is Philadelphia chromosome positive chronic myeloid. In one embodiment, the cancer is Philadelphia chromosome positive acute lymphoblastic leukemias. In one embodiment, the cancer is acute myeloid leukemias. In one embodiment, the cancer is myeloproliferative neoplasms, such as Polycythemia Vera, Essential Thrombocythemia and Primary Myelofibrosis. In one embodiment, the cancer is selected from the group consisting of Polycythemia Vera, Essential Thrombocythemia and Primary Myelofibrosis. In one embodiment, the cancer is Polycythemia Vera. In one embodiment, the cancer is Essential Thrombocythemia. In one embodiment, the cancer is Primary Myelofibrosis. In one embodiment, the cancer is breast cancer. In one embodiment, the cancer is lung cancer. In one embodiment, the cancer is liver cancer. In one embodiment, the cancer is colorectal cancer. In one embodiment, the cancer is esophageal cancer. In one embodiment, the cancer is gastric cancer. In one embodiment, the cancer is squamous-cell carcinoma of the head and neck. In one embodiment, the cancer is glioblastoma. In one embodiment, the cancer is anaplastic large-cell lymphoma. In one embodiment, the cancer is thyroid carcinoma. In one embodiment, the cancer is spitzoid neoplasms. In one embodiment, the cancer is selected from the group consisting of NSCLC, a colon cancer, an esophageal cancer, a rectal cancer, juvenile myelomonocytic leukemia ("JMML"), breast cancer, melanoma, and a pancreatic cancer.

In one embodiment, the abnormal cell growth is cancer mediated by SHP2.

In one embodiment, the abnormal cell growth is cancer which may be treated by a SHP2 inhibitor. In a further embodiment, the abnormal cell growth is cancer that responds to treatment with a SHP2 inhibitor.

In one embodiment, the abnormal cell growth comprises a cell containing a mutation encoding the KRASG12C variant. See WO 2019/051084.

In one embodiment, the abnormal cell growth is a disease or disorder comprising a cell with a mutation encoding an NF1 loss of function ("NF1LOF") variant. In one embodiment, the NF1 mutation is a loss of function mutation. In one embodiment, the disease or disorder is a tumor comprising cells with an NF1 loss of function mutation. In one embodiment, the tumor is an NSCLC or melanoma tumor. In one embodiment, the disease is selected from neurofibromatosis type I, neurofibromatosis type II, schwannomatosis, and Watson syndrome.

In one embodiment, the abnormal cell growth is associated with a RAS pathway mutation in a cell of the subject that renders the cell at least partially dependent on signaling flux through SHP2. In one embodiment, the RAS pathway mutation is a RAS mutation selected from a KRAS mutation, an NRAS mutation, a SOS mutation, a BRAF Class III mutation, a Class I MEKI mutation, a Class II MEKI mutation, and an F1 mutation. In one embodiment, the KRAS mutation is selected from a $KRAS^{G12A}$ mutation, a $KRAS^{G12C}$ mutation, a $KRAS^{G12D}$ mutation, a $KRAS^{G12F}$ mutation, a $KRAS^{G12I}$ mutation, a $KRAS^{G12L}$ mutation, a $KRAS^{G12R}$ mutation, a $KRAS^{G12S}$ mutation, a $KRAS^{G12V}$ mutation, and a $KRAS^{G12Y}$ mutation. In one embodiment, the KRAS mutation is a $KRAS^{G12A}$ mutation. In one embodiment, the KRAS mutation is a $KRAS^{G12C}$ mutation. In one embodiment, the KRAS mutation is a $KRAS^{G12D}$ mutation. In one embodiment, the KRAS mutation is a $KRAS^{G12F}$ mutation. In one embodiment, the KRAS mutation is a $KRAS^{G12I}$ mutation. In one embodiment, the KRAS mutation is a $KRAS^{G12L}$ mutation. In one embodiment, the KRAS mutation is a $KRAS^{G12R}$ mutation. In one embodiment, the KRAS mutation is a $KRAS^{G12S}$ mutation. In one embodiment, the KRAS mutation is a $KRAS^{G12V}$ mutation. In one embodiment, the KRAS mutation is a $KRAS^{G12Y}$ mutation. In one embodiment, the BRAF Class III mutation is selected from one or more of the following amino acid substitutions in human BRAF: D287H; P367R; V459L; G466V; G466E; G466A; S467L; G469E; N581S; N581I; D594N; D594G; D594A; D594H; F595L; G596D; G596R and A762E. In one embodiment, the Class I MEKI mutation is selected from one or more of the following amino acid substitutions in human MEKI: D67N; P124L; P124S; and L177V. In one embodiment, the Class II MEKI mutation is selected from one or more of the following amino acid substitutions in human MEKI: AE51-Q58; AF53-Q58; E203K; L177M; C121S; F53L; K57E; Q56P; and K57N.

In one embodiment, the abnormal cell growth is selected from the group consisting of ALK- or ROS1-positive non-small cell lung cancer, B-type Raf proto-oncogene V600E mutation colorectal cancer, or RAS-mutant, NF1-mutant or BRAF class 3-mutant solid tumors. In one embodiment, the abnormal cell growth is ALK-positive non-small cell lung cancer. In one embodiment, the abnormal cell growth is ROS1-positive non-small cell lung cancer. In one embodiment, the abnormal cell growth is B-type Raf proto-oncogene V600E mutation colorectal cancer. In one embodiment, the abnormal cell growth is RAS-mutant solid tumors. In one embodiment, the abnormal cell growth is NF1-mutant solid tumors. In one embodiment, the abnormal cell growth is BRAF class 3-mutant solid tumors.

In one embodiment, the hemihydrate crystalline form of (S)-1'-(6-((2-amino-3-chloropyridin-4-yl)thio)-1,2,4-triazin-3-yl)-1,3-dihydrospiro[indene-2,4'-piperidin]-1-amine free base (Form 1) is used in combination with one or more additional pharmaceutical compounds. In one embodiment, the additional pharmaceutical compound(s) is selected from the group consisting of lorlatinib, binimetinib, cetuximab, and encorafenib. In one embodiment, the additional pharmaceutical compound is lorlatinib. In one embodiment, the additional pharmaceutical compounds are encorafenib and cetuximab. In one embodiment, the additional pharmaceutical compound is binimetinib.

EXAMPLES

The examples and preparations provided below further illustrate and exemplify particular aspects and embodiments of the invention. It is to be understood that the scope of the present invention is not limited by the scope of the following examples.

Example 1

Amorphous (S)-1'-(6-((2-amino-3-chloropyridin-4-yl)thio)-1,2,4-triazin-3-yl)-1,3-dihydrospiro[indene-2,4'-piperidin]-1-amine (R)—N—((S)-1'-(6-((2-Amino-3-chloropyridin-4-yl)thio)-1,2,4-triazin-3-yl)-1,3-dihydrospiro[indene-2,4'-piperidin]-1-yl)-2-methylpropane-2-sulfinamide (20 mg, 0.037 mmol) was diluted with dioxane (1 mL), followed by the addition of HCl (92 μL, 0.37 mmol). After stirring for 30 minutes, the reaction was diluted with dichloromethane ("DCM") and saturated aqueous sodium bicarbonate. After stirring the mixture for 10 minutes, the layers were separated, and the DCM was dried over $MgSO_4$, filtered and concentrated. The material was purified on silica gel eluting with 20% methanol/ethyl acetate to afford amorphous (S)-1'-(6-((2-amino-3-chloropyridin-4-yl)thio)-1,2,4-triazin-3-yl)-1,3-dihydrospiro[indene-2,4'-piperidin]-1-amine (15 mg, 0.034 mmol, 93% yield). $^1H$ NMR (400 MHZ, $CDCl_3$) δ8.2 (s, 1H), 7.76 (d, 1H, J=5.2 Hz), 7.2-7.35 (m, 4H), 6.15 (d, 1H, J=5.2 Hz), 4.92 (br, 2H), 4.78 (br, 1H), 4.01 (s, 1H), 3.37 (m, 2H), 3.14 (d, 1H, J=15.6 Hz), 2.78 (d, 1H, J=15.6), 1.3-1.91 (m, 7H); m/z (esi/APCI) $M^+1$=440.1.

Example 2

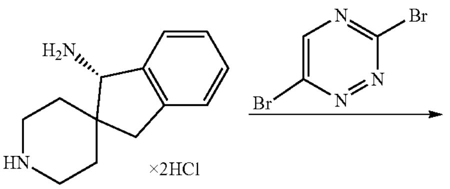

-continued

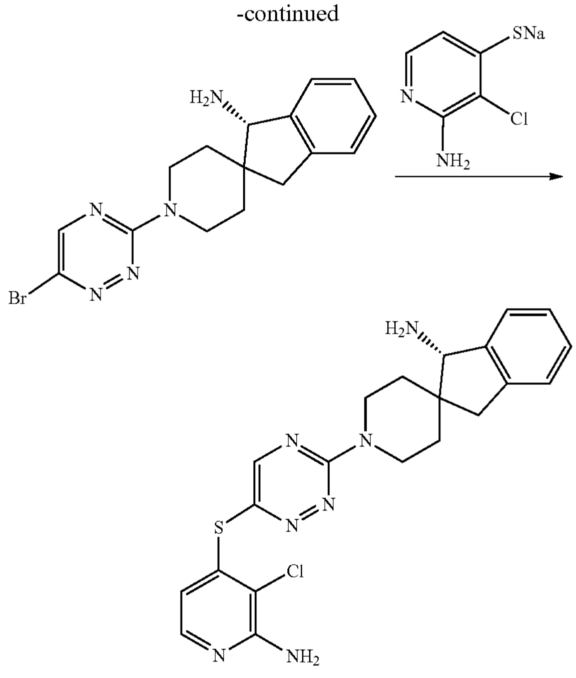

Crystalline (S)-1'-(6-((2-amino-3-chloropyridin-4-yl)thio)-1,2,4-triazin-3-yl)-1,3-dihydrospiro[indene-2,4'-piperidin]-1-amine free base hemihydrate (Form 1)

(S)-1,3-Dihydrospiro[indene-2,4'-piperidin]-1-amine dihydrochloride (3.89 Kg) and 3,6-dibromo-1,2,4-triazine (3.71 Kg) were reacted with triethylamine (6.45 Kg) in 1,4-dioxane (34.3 Kg) at about 20-30° C. to provide (S)-1'-(6-bromo-1,2,4-triazin-3-yl)-1,3-dihydrospiro[indene-2,4'-piperidin]-1-amine in situ. (S)-1'-(6-Bromo-1,2,4-triazin-3-yl)-1,3-dihydrospiro[indene-2,4'-piperidin]-1-amine was reacted with sodium 2-amino-3-chloropyridine-4-thiolate (3.08 Kg), and the mixture was heated to about 70-75° C. for about 12.5 hours to provide (S)-1'-(6-((2-amino-3-chloropyridin-4-yl)thio)-1,2,4-triazin-3-yl)-1,3-dihydrospiro[indene-2,4'-piperidin]-1-amine. The mixture was cooled to about 15-30° C. Celite® (1.95 Kg) was added to the reaction at about 15-30° C. and stirred for about 1 hour, and the slurry was filtered and rinsed with 1,4-dioxane. A solvent swap was performed to replace 1,4-dioxane with tetrahydrofuran. Crude (S)-1'-(6-((2-amino-3-chloropyridin-4-yl)thio)-1,2,4-triazin-3-yl)-1,3-dihydrospiro[indene-2,4'-piperidin]-1-amine was purified by chromatography on silica gel (pre-treated with isopropyl alcohol) using mixtures of dichloromethane, methanol, ethanol, n-hexane and triethylamine as the eluent. After chromatography, the product was crystallized from methanol and water to afford purified crystalline (S)-1'-(6-((2-amino-3-chloropyridin-4-yl)thio)-1,2,4-triazin-3-yl)-1,3-dihydrospiro[indene-2,4'-piperidin]-1-amine free base hemihydrate (Form 1) (1.39 Kg).

Powder X-ray diffraction analysis was conducted using a Bruker AXS D8 Endeavor diffractometer equipped with a Copper (Cu) radiation source. The divergence slit was set at 15 mm continuous illumination. Diffracted radiation was detected by a PSD-Lynx Eye detector, with the detector PSD opening set at 2.99 degrees. The X-ray tube voltage and amperage were set to 40 kV and 40 mA respectively. Data was collected in the Theta-Theta goniometer at the Cu wavelength ($CuK_\alpha$=1.5418λ) from 3.0 to 40.0 degrees 2-Theta using a step size of 0.00998 degrees and a step time of 1.0 second. The anti-scatter screen was set to a fixed distance of 3.0 mm. Samples were rotated at 15/min during collection. Samples were prepared by placing them in a silicon low background sample holder and rotated during collection. Data were collected using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of ≥3% were generally chosen. Typically, the peaks which were not resolved or were consistent with noise were not selected. A typical error associated with the peak position from PXRD stated in USP up to +/−0.2° 2-Theta (USP-941).

The PXRD pattern of Example 2, free base hemihydrate Form 1 is shown in FIG. 1. A PXRD peak list and relative intensity data for the compound of Example 2, free base hemihydrate Form 1 (2-Theta °) is provided in Table 1 below:

TABLE 1

| Angle (2 theta °) ± 0.2° 2θ | Relative Intensity (%) |
|---|---|
| 5.4 | 6.8 |
| 10.9 | 60.1 |
| 12.1 | 5.2 |
| 13.5 | 3.4 |
| 14.0 | 40.2 |
| 15.4 | 54.9 |
| 15.5 | 44.5 |
| 16.0 | 61.8 |
| 16.4 | 23.1 |
| 17.2 | 49.8 |
| 17.7 | 16.5 |
| 19.0 | 19.1 |
| 19.3 | 45.5 |
| 19.6 | 41.2 |
| 19.7 | 41.5 |
| 20.5 | 39.6 |
| 21.8 | 33.4 |
| 22.2 | 15.0 |
| 22.5 | 100.0 |
| 23.5 | 5.5 |
| 24.3 | 18.4 |
| 25.1 | 68.5 |
| 25.4 | 5.3 |
| 25.7 | 12.5 |
| 26.0 | 7.2 |
| 26.8 | 13.9 |
| 27.1 | 51.2 |
| 27.3 | 50.9 |
| 27.8 | 11.6 |
| 28.2 | 71.3 |
| 29.3 | 16.6 |
| 29.5 | 41.5 |
| 30.0 | 5.6 |
| 31.5 | 12.6 |
| 31.9 | 3.9 |
| 32.2 | 9.9 |
| 33.2 | 12.1 |
| 33.3 | 10.0 |
| 33.9 | 4.5 |
| 34.1 | 5.7 |
| 34.7 | 7.4 |
| 35.2 | 11.7 |
| 35.4 | 12.6 |

TABLE 1-continued

| Angle (2 theta °) ± 0.2° 2θ | Relative Intensity (%) |
|---|---|
| 36.1 | 5.9 |
| 36.9 | 3.3 |
| 37.2 | 5.0 |
| 37.5 | 3.2 |
| 38.0 | 5.6 |
| 38.6 | 3.5 |
| 39.0 | 4.5 |

The characteristic PXRD peak list and relative intensity data for the compound of Example 2, free base hemihydrate Form 1 (2-Theta °) is provided in Table 2 below:

TABLE 2

| Angle (°2-Theta) ± 0.2° 2θ | Relative Intensity (%) |
|---|---|
| 10.9 | 60.1 |
| 16.0 | 61.8 |
| 14.0 | 40.2 |
| 15.4 | 54.9 |
| 15.5 | 44.5 |
| 25.1 | 68.5 |
| 20.5 | 39.6 |
| 29.5 | 41.5 |

Solid-state NMR ("ssNMR") analysis was conducted on a cross-polarization magic angle spinning ("CPMAS") probe positioned into a Bruker-BioSpin Avance III 500 MHz ($^1H$ frequency) NMR spectrometer. Material was packed into a 4 mm $ZrO_2$ rotor. A magic angle spinning rate of 14.0 kHz was used. Spectra were collected at ambient temperature (temperature uncontrolled).

$^{13}C$ ssNMR spectrum were collected using a proton decoupled CPMAS experiment. A phase modulated proton decoupling field of 80-100 kHz was applied during spectral acquisition. The cross-polarization contact time was set to 2 ms and the recycle delay to 11.4 seconds. The number of scans was adjusted to obtain an adequate signal to noise ratio. The $^{13}C$ chemical shift scale was referenced using a $^{13}C$ CPMAS experiment on an external standard of crystalline adamantane, setting its up-field resonance to 29.5 ppm.

Automatic peak picking was performed using Bruker-BioSpin TopSpin version 3.6 software. Generally, a threshold value of 5% relative intensity was used for preliminary peak selection. The output of the automated peak picking was visually checked to ensure validity and adjustments were manually made if necessary. Although specific solid-state NMR peak values are reported herein there does exist a range for these peak values due to differences in instruments, samples, and sample preparation. This is common practice in the art of solid-state NMR because of the variation inherent in peak positions. A typical variability for a $^{13}C$ chemical shift x-axis value is on the order of plus or minus 0.2 ppm for a crystalline solid. The solid-state NMR peak heights reported herein are relative intensities. Solid-state NMR intensities can vary depending on the actual setup of the CPMAS experimental parameters and the thermal history of the sample.

For crystalline (S)-1'-(6-((2-amino-3-chloropyridin-4-yl)thio)-1,2,4-triazin-3-yl)-1,3-dihydrospiro[indene-2,4'-piperidin]-1-amine free base hemihydrate (Form 1), five characteristic peaks were identified: $^{13}C$ chemical shifts at 44.4, 47.7, 149.2, 36.6, and 26.9±0.2 ppm.

The $^{13}C$ ssNMR spectrum of Example 2, free base hemihydrate Form 1 is shown in FIG. 2. The $^{13}C$ ssNMR spectrum of Example 2, free base hemihydrate Form 1 (ppm) is provided in Table 3 below:

TABLE 3

| $^{13}C$ Chemical Shift (ppm) ± 0.2 ppm | Relative Intensity (%) |
|---|---|
| 26.9 | 51 |
| 33.8 | 39 |
| 35.0 | 59 |
| 36.6 | 37 |
| 39.0 | 82 |
| 39.4 | 67 |
| 40.2 | 67 |
| 41.3 | 38 |
| 43.4 | 81 |
| 44.4 | 74 |
| 47.7 | 63 |
| 66.0 | 49 |
| 68.9 | 38 |
| 109.0 | 93 |
| 124.5 | 100 |
| 127.0 | 41 |
| 127.9 | 70 |
| 128.9 | 51 |
| 129.8 | 43 |
| 139.7 | 88 |
| 140.9 | 48 |
| 145.1 | 57 |
| 145.4 | 79 |
| 146.5 | 39 |
| 149.2 | 49 |
| 154.5 | 48 |
| 155.9 | 64 |
| 158.9 | 38 |

Raman spectra were collected using a Thermo Scientific iS50 FT-Raman accessory attached to the FT-IR bench. A CaF2 beam splitter is utilized in the FT-Raman configuration. The spectrometer is equipped with a 1064 nm diode laser and a room temperature InGaAs detector. Prior to data acquisition, instrument performance and calibration verifications were conducted using polystyrene. Samples were analyzed in glass NMR tubes, as tablets or in a suitable sample holder held static during data collection. The spectra were collected using between 0.1 and 0.5 W of laser power and 512 co-added scans. The collection range was 3700-100 $cm^{-1}$. The API spectra were recorded using 2 $cm^{-1}$ resolution, and Happ-Genzel apodization was utilized for all of the spectra. Multiple spectra were recorded, and the reported spectrum is representative of two spots.

The intensity scale was normalized to 1 prior to peak picking. Peaks were manually identified using the Thermo Nicolet Omnic 9.7.46 software. Peak position was picked at the peak maximum, and peaks were only identified as such, if there was a slope on each side; shoulders on peaks were not included. For neat free base hemihydrate Form 1 an absolute threshold of 0.006 with a sensitivity of 75 was utilized during peak picking. The peak position has been rounded to the nearest whole number using standard practice (0.5 rounds up, 0.4 rounds down). Peaks with normalized peak intensity between (1-0.75), (0.74-0.30), (0.29-0) were labeled as strong, medium, and weak, respectively.

The FT-Raman spectrum of Example 2, free base hemihydrate Form 1, is shown in FIG. 3. A FT-Raman spectrum wavenumber values list and normalized intensity data for the compound of Example 2, free base hemihydrate Form 1 ($cm^{-1}$) is provided in Table 4 below:

TABLE 4

| Peak Position ($cm^{-1}$) ± 0.2 $cm^{-1}$ | Normalized Intensity | Classification |
|---|---|---|
| 210 | 0.33 | m |
| 227 | 0.40 | m |
| 246 | 0.25 | w |
| 281 | 0.45 | m |
| 320 | 0.26 | w |
| 377 | 0.14 | w |
| 402 | 0.25 | w |
| 421 | 0.13 | w |
| 432 | 0.13 | w |
| 448 | 0.13 | w |
| 486 | 0.32 | m |
| 495 | 0.28 | w |
| 512 | 0.19 | w |
| 543 | 0.13 | w |
| 555 | 0.21 | w |
| 607 | 0.69 | m |
| 649 | 0.22 | w |
| 654 | 0.20 | w |
| 719 | 0.27 | w |
| 727 | 0.16 | w |
| 747 | 0.15 | w |
| 780 | 0.52 | m |
| 803 | 0.29 | w |
| 868 | 0.04 | w |
| 896 | 0.06 | w |
| 919 | 0.16 | w |
| 931 | 0.19 | w |
| 948 | 0.09 | w |
| 967 | 0.13 | w |
| 1022 | 0.62 | m |
| 1051 | 0.52 | m |
| 1084 | 0.36 | m |
| 1109 | 0.18 | w |
| 1134 | 0.75 | s |
| 1156 | 0.43 | m |
| 1202 | 0.23 | w |
| 1210 | 0.30 | m |
| 1231 | 0.38 | m |
| 1260 | 0.37 | m |
| 1267 | 0.32 | m |
| 1286 | 0.15 | w |
| 1305 | 0.14 | w |
| 1322 | 0.32 | m |
| 1362 | 0.23 | w |
| 1379 | 0.10 | w |
| 1431 | 0.24 | w |
| 1435 | 0.24 | w |
| 1462 | 0.58 | m |
| 1529 | 1.00 | s |
| 1573 | 0.21 | w |
| 1587 | 0.23 | w |
| 1609 | 0.26 | w |
| 1904 | 0.02 | w |
| 2166 | 0.04 | w |
| 2379 | 0.02 | w |
| 2517 | 0.02 | w |
| 2701 | 0.02 | w |
| 2749 | 0.03 | w |
| 2843 | 0.26 | w |
| 2859 | 0.28 | w |
| 2881 | 0.19 | w |
| 2900 | 0.23 | w |
| 2925 | 0.45 | m |
| 2986 | 0.11 | w |
| 3016 | 0.41 | m |
| 3045 | 0.35 | m |
| 3077 | 0.28 | w |
| 3172 | 0.08 | w |
| 3280 | 0.14 | w |
| 3296 | 0.12 | w |
| 3334 | 0.09 | w |
| 3456 | 0.01 | w |
| 3512 | 0.02 | w |

The characteristic FT-Raman wavenumber ($cm^{-1}$) values list and normalized intensity data for the compound of Example 2, free base hemihydrate Form 1 ($cm^{-1}$) is provided in Table 5 below:

TABLE 5

| Peak Position ($cm^{-1}$) | Normalized Intensity | Classification |
|---|---|---|
| 607 | 0.69 | m |
| 1462 | 0.58 | m |
| 1051 | 0.52 | m |
| 1573 | 0.21 | w |

Example 3

Comparative Analysis Between Crystalline (S)-1'-(6-((2-amino-3-chloropyridin-4-yl)thio)-1,2,4-triazin-3-yl)-1,3-dihydrospiro[indene-2,4'-piperidin]-1-amine Free Base Hemihydrate Form 1 and Amorphous (S)-1'-(6-((2-amino-3-chloropyridin-4-yl)thio)-1,2,4-triazin-3-yl)-1,3-dihydrospiro[indene-2,4'-piperidin]-1-amine The chemical stability data using HPLC was evaluated on samples stored at several conditions as listed in Table 6 between free base hemihydrate Form 1 and amorphous form.

HPLC Method

Column: LC\027 Agilent Poroshell 120 EC-C18 150×4.6 mm, 2.7 μm

Column Temperature: 40° C.

Autosampler Temperature: Ambient

UV wavelength: 220 nm

Injection Volume: 4.00 μL

Flow Rate: 1.5 mL/min

Mobile Phase A: 0.02% TFA in H2O

Mobile Phase B: 0.02% TFA in MeCN

Time (minutes) Solvent B [%]

0 20

3 20

15 70

15.1 95

16 95

16.1 20

20.0 20

TABLE 6

| Starting material | Conditions | Observations after 7 days | PXRD after 7 days | HPLC purity (%) after 7 days |
|---|---|---|---|---|
| Amorphous | 25° C./ 60% RH | Vibrant yellow | Amorphous | 82.8 |
| Amorphous | 40° C./ 75% RH | Vibrant yellow | Amorphous | 86.7 |
| Amorphous | 80° C. | Brown | Amorphous | 54.7 |
| Amorphous | Ambient | Vibrant yellow | Amorphous | 71.7 |
| Form 1 | 25° C./ 60% RH | Yellow | Form 1 | 97.5 |
| Form 1 | 40° C./ 75% RH | Yellow | Form 1 | 97.6 |
| Form 1 | 80° C. | Yellow | Form 1 | 97.1 |
| Form 1 | Ambient | Yellow | Form 1 | 97.1 |

All publications and patent applications cited in the specification are herein incorporated by reference in their entirety. It will be apparent to those of ordinary skill in the art that certain changes and modifications may be made thereto without departing from the spirit or scope of the appended claims.

The invention claimed is:

1. A hemihydrate crystalline form of(S)-1'-(6-((2-amino-3-chloropyridin-4-yl)thio)-1,2,4-triazin-3-yl)-1,3-dihydrospiro[indene-2,4'-piperidin]-1-amine free base characterized by a PXRD pattern comprising characterizing peaks at 2θ values of 10.9, 14.0, 15.4, and 16.0±0.2° 2θ.

2. The hemihydrate crystalline form of claim 1, further characterized by a $^{13}C$ ssNMR spectrum comprising resonance (ppm) values of 44.4, 47.7, 149.2, and 36.6=0.2 ppm.

3. The hemihydrate crystalline form of claim 1, further characterized by a FT-Raman spectrum comprising wavenumber ($cm^{-1}$) values of 607, 1462, 1051, and 1573±0.2 $cm^{-1}$.

4. The hemihydrate crystalline form of claim 1, wherein the PXRD pattern further comprises a peak at the 2θ value of: 25.1=0.2° 2θ.

5. The hemihydrate crystalline form of claim 1, wherein the PXRD pattern further comprises a peak at the 2θ value of: 20.5±0.2° 2θ.

6. The hemihydrate crystalline form of claim 1, wherein the PXRD pattern further comprises a peak at the 2θ value of: 29.5±0.2° 2θ.

7. The hemihydrate crystalline form of claim 2, wherein the $^{13}C$ ssNMR spectrum further comprises a resonance (ppm) value of 26.9=0.2 ppm.

8. The hemihydrate crystalline form of claim 1, comprising less than 3% by weight of any other physical forms of(S)-1'-(6-((2-amino-3-chloropyridin-4-yl)thio)-1,2,4-triazin-3-yl)-1,3-dihydrospiro[indene-2,4'-piperidin]-1-amine.

9. A pharmaceutical composition, comprising:

the hemihydrate crystalline form of claim 1; and at least one pharmaceutically acceptable excipient.

10. A method of treating cancer in subject in need thereof, the method comprising:

administering to the subject a therapeutically effective amount of the hemihydrate crystalline form of claim 1, wherein the subject is a human having cancer or diagnosed with cancer, and wherein the cancer is non-small cell lung cancer or colorectal cancer.

11. The method, of claim 10, wherein the cancer is selected from the group consisting of ALK-positive non-small cell lung cancer, ROS1-positive non-small cell lung cancer, or B-type Raf proto-oncogene V600E mutation colorectal cancer.

12. The method of claim 10, further comprising:

administering one or more additional pharmaceutical compounds in combination with the hemihydrate crystalline form of claim 1.

13. The method of claim 12, wherein the additional pharmaceutical compound is selected from the group consisting of lorlatinib, binimetinib, cetuximab, and encorafenib.

14. The hemihydrate crystalline form of claim 2, further characterized by a FT-Raman spectrum comprising wavenumber ($cm^{-1}$) values of 607, 1462, 1051, and 1573±0.2 $cm^{-1}$.

* * * * *